United States Patent [19]
Adams et al.

[11] Patent Number: 5,441,518
[45] Date of Patent: Aug. 15, 1995

[54] IMPLANTABLE CARDIOVERTER DEFIBRILLATOR SYSTEM HAVING INDEPENDENTLY CONTROLLABLE ELECTRODE DISCHARGE PATHWAY

[75] Inventors: Theodore P. Adams, Edina; Charles G. Supino, Arden Hills; Mark W. Kroll, Minnetonka, all of Minn.

[73] Assignee: Angeion Corporation, Plymouth, Minn.

[21] Appl. No.: 96,170

[22] Filed: Jul. 22, 1993

[51] Int. Cl.$^6$ ............................................... A61N 1/39
[52] U.S. Cl. ................................................................ 607/5
[58] Field of Search ........................................ 607/5, 4

[56] References Cited

U.S. PATENT DOCUMENTS

| | | |
|---|---|---|
| 4,708,145 | 11/1987 | Tacker et al. . |
| 4,727,877 | 3/1988 | Kallok ............................ 607/5 |
| 4,800,883 | 1/1989 | Winstrom . |
| 4,821,723 | 4/1989 | Baker, Jr. et al. . |
| 4,969,463 | 11/1990 | Dahl et al. ...................... 607/5 |
| 4,998,531 | 3/1991 | Bocchi et al. ................... 607/5 |
| 5,107,834 | 4/1992 | Ideker et al. . |
| 5,163,427 | 11/1992 | Keimel ............................ 607/4 |
| 5,199,429 | 4/1993 | Kroll et al. ..................... 607/5 |
| 5,209,229 | 5/1993 | Gilli ............................... 607/5 |
| 5,306,291 | 4/1994 | Kroll et al. . |

*Primary Examiner*—William E. Kamm
*Assistant Examiner*—Kennedy J. Schaetzle
*Attorney, Agent, or Firm*—Patterson & Keough

[57] ABSTRACT

An implantable multichamber cardioversion and defibrillation system is provided with multiple independently controllable and programmable switched electrode discharge pathways. This independently controlled switching arrangement provides for control over the polarity, phase, direction and timing of all cardioversion and defibrillation countershocks, and allows for the varying of subsequent countershocks after an initial countershock. The switching arrangement is, preferably, both programmable prior to implantation of the system and re-programmable after implantation of the system.

28 Claims, 6 Drawing Sheets

IMPLANTABLE CARDIOVERTER DEFIBRILLATOR SYSTEM HAVING INDEPENDENTLY CONTROLLABLE ELECTRODE DISCHARGE PATHWAY

CROSS REFERENCES TO CO-PENDING APPLICATIONS

This patent application relates to U.S. patent application entitled OPTIMAL ENERGY STEERING FOR AN IMPLANTABLE DEFIBRILLATOR, Ser. No. 07/841,544, filed Feb. 26, 1992 now U.S. Pat. No. 5,306,291; U.S. patent application entitled SUCCESSIVE CHANGEABLE DEFIBRILLATION WAVEFORMS, Ser. No. 07/856,982, filed Mar. 24, 1992; and U.S. patent application entitled ATRIAL CARDIOVERTER WITH VENTRICULAR PROTECTION, Ser. No. 08/020,573, filed Feb. 22, 1993.

BACKGROUND

1. Field of the Invention

The present invention relates generally to implantable cardioverter defibrillator systems for treatment of multichamber cardiac dysrhythmias including fibrillation. More particularly, the present invention relates to the independent selection and control of multiple implantable electrode discharge pathways through which multichamber cardioversion or defibrillation countershocks are delivered.

2. Background of the Invention

Cardiac muscle fibrillation is the rapid and asynchronous contraction of individual muscle fibers in the heart. The result is a slightly quivering and non-functional heart muscle. When fibrillation occurs within the lower chambers of the heart or ventricles, blood flow ceases and, if not corrected within minutes, will result in death of the patient. Fibrillation occurring only in the upper chambers of heart or atria results in a diminution of cardiac output that may be symptomatic to the patient. Other forms of cardiac dysrhythmia include ventricular or supraventricular tachycardia which are very rapid organized/synchronous muscle fiber contractions, that impair cardiac output to lesser or greater degrees dependent on cardiac refill times and preload pressures.

Implantable cardioverter and defibrillator systems accomplish the desired treatment of cardiac dysrhythmia by passing a cardioversion or defibrillation countershock through the heart muscle depending on the type of cardiac dysrhythmia diagnosed. An objective of the cardioversion or defibrillation countershock is to immerse as much of the myocardium as possible within the electrical field generated by the countershock. The countershock is a truncated capacitive discharge of electrical energy that generally ranges from 0.1 to 5.0 Joules for cardioversion and from 5 to 40 Joules for defibrillation of the ventricles.

One of the problems in treating cardiac dysrhythmias using cardioversion or defibrillation countershocks is that the strength, and hence the effectiveness, of the electrical field generated across the myocardium may vary greatly. As with any electrical discharge, the electrical field generated by a cardioversion or defibrillation countershock will be a function of the amount and waveform shape of the electrical energy discharged, the location and orientation of the electrodes forming a discharge pathway through which the electrical energy is discharged and the transmicivity or resistivity of the medium through which the electrical field is generated. For electrical cardiac stimulation internal to a human patient, there are a number of viable positions in the patient where implantable discharge electrodes may be positioned.

Various ICD systems employ implantable electrodes positioned external to the heart. These electrodes are placed on the epicardial surface or on the pericardial sac. While these epicardial electrodes are effective in delivering a desired defibrillation countershock, major surgery is required in order to gain access to the epicardium and pericardium for attachment of these electrodes.

Implanted electrodes using vascular access are easier to implant within the heart chambers. These intravenous electrodes are carried on catheters and inserted via venipuncture into the subclavian vein and threaded through the superior vena cava into the right atrium and right ventricle. Intravenous electrodes can be placed at all levels, even passing below the heart into the inferior vena cava.

A third approach uses subcutaneous patches. This method employs tunneling and placement of an appropriate patch electrode within the subcutaneous space requiring minimal surgery. The anatomy of the subcutaneous space provides for placement of a patch electrode virtually anywhere. Effective results for such subcutaneous electrodes have been achieved with placement at the left anterolateral chest wall, epigastrium and left upper quadrant of the abdominal wall.

Various ICD systems contemplate using combinations of electrodes such as those described in U.S. Pat. No. 4,708,145 issued to Tacker, et al. and U.S. Pat. No. 5,107,834 issued to Dahl, et al. These systems employ basic switching mechanisms that generate countershock pulses across a preset combination of electrodes and corresponding discharge pathways, such as firing a pulse across a first set of electrodes and then firing a pulse across a second set of electrodes. In both of these systems, however, the combination of electrodes is predetermined and fixed once the ICD is implanted. The same sequence of switch settings is always used, leading to identical pulses being generated repetitively across the same discharge pathways.

The use of a preset combination of electrodes for cardioversion or defibrillation countershocks also constrains where the electrodes can be placed, even in those systems relying upon multiple electrode placement. For example, in an ICD system with four electrodes: a, b, c and d; if the preset combination of electrodes is a first discharge pathway between electrodes a and b and a second discharge pathway between electrodes c and d, then electrode a must be generally across the myocardium from electrode b, and electrode c must be generally across the myocardium from electrode d. Obviously, the implantation sites for electrodes a, b, c and d must be chosen carefully ahead of time to ensure adequate immersion of the myocardium within the electric field of the countershock.

Another group of ICD systems disclose multiple electrodes with polarity reversing switch mechanisms, such as U.S. Pat. No. 4,800,883 issued to Winstrom, U.S. Pat. No. 4,821,723 issued to Baker, et al., and U.S. Pat. No. 4,998,531 issued to Bocchi, et al. These systems teach monophasic, bi-phasic, multiphasic and even temporally sequential countershock pulses generated across differing sets of electrodes and discharge pathways. Again, however, in each of these systems the differing sets of electrodes used to deliver the countershocks are preset before the ICD is implanted. Regardless of whether the countershock is a mono-, bi-, or multi-phased pulse, the countershock is delivered through the same set of electrodes every time.

Although the use of multiple sets of implanted electrodes located in different positions relative to the heart has provided for several variations in the discharge pathways, and hence the types of electrical fields, that can be generated across the myocardium by a cardioversion or defibrillation countershock, the number and variety of electrical fields are presently limited by the preset combinations of electrodes and discharge pathways available in existing ICD systems. While the number and variety of electrical fields generated by these preset combination of electrodes and discharge pathways are successful in treating many cardiac dysrhythmias, it would be advantageous to provide an ICD with more flexibility in generating a wider variety of discharge pathways and corresponding electrical fields to treat cardiac dysrhythmias.

SUMMARY OF THE INVENTION

The present invention is an implantable cardioverter defibrillator (ICD) system for multichamber cardiac cardioversion and defibrillation having independently controllable electrode discharge pathways. The ICD system of the present invention is capable of selectively configuring three or more implantable electrodes into a wide variety of discharge pathways for the electrical field of a cardioversion or defibrillation countershock. Each implantable electrode is selectively and independently electrically connected by a programmable switching network to a discharge capacitor system in the ICD system such that any given electrode can be configured as either the cathode or anode in relation to any other or all other electrodes. The programmable switching network can also selectively control the duration, number and polarity of pulses which make up each cardioversion or defibrillation countershock waveform. The independently controllable discharge pathways allow for uniquely tailored delivery of cardioversion or defibrillation countershocks to treat cardiac dysrhythmias in any of the chambers of the heart.

In the present invention, initial control for delivering cardioversion or defibrillation countershocks is pre-programmed. Depending upon the type of cardiac dysrhythmia detected, the programming information is used to configure switch states within the programmable switching network by either closing; or opening selected independently operated electrode switches. This control in configuring the multiple independently switched discharge pathways allows the ICD system of the present invention great latitude in choosing which electrodes will be used, the polarity the countershock current will have, and how long each pulse of the cardioversion or defibrillation waveform will be delivered through that discharge pathway. Additionally, by reversing the polarity during a delivered countershock, the pulse phase can be altered, thereby increasing the flexibility of the ICD system.

The ICD system of the present invention is also designed to accept program changes after implantation. These changes to the programming are then followed during subsequent defibrillation therapy. Alternatively, the ICD system will accept real time control from a physician operator at the patient bedside. External communication with the ICD system can employ a number of modalities utilizing ultrasound, magnetic, radio frequency radiation, visible and invisible radiation signals. The flexibility in program control utilizing the programmable switching network of the ICD system facilitates the physician in customizing the ICD system response to best meet the specific needs of the individual patient.

An object of the present invention is to provide an ICD system with programmability and re-programmability of an independently controlled discharge electrode switching network to allow for modification of waveform polarity, multiplicity of phase, duration of pulse and direction of the cardioversion or defibrillation countershocks. Such an ICD system takes out much of the guess work and need for pre-implantation electrophysiologic studies inherent in using other systems that have to predict, in advance, electrode placement and pulse form generated. The flexibility of the present invention achieves maximum selectivity and provides a uniformly manufactured ICD system thereby avoiding ICD systems that have been averaged so as to work in a greater number of potential patients. The flexibility of the present invention also allows a single ICD to be optimized for dual chamber cardioversion or defibrillation of either the atria or ventricles or both.

In accordance, with the present invention, a method and apparatus are provided for delivering multichamber cardiac cardioversion or defibrillation countershocks having atrial and ventricular sensing leads implanted within the respective chambers, multiple discharge electrodes implanted within the heart chambers and without the heart in the proximate vasculature and subcutaneous spaces of the thoracic and abdominal wall, logic and timing circuitry, charging circuitry and a system of independently controlled discharge electrode switches capable of providing variable combinations of electrical configurations thereby altering pulse polarity, phase, duration, sequencing and direction of the cardioversion or defibrillation countershocks.

DETAILED DESCRIPTION OF THE PREFERRED EMBODIMENT

Figure 1A:
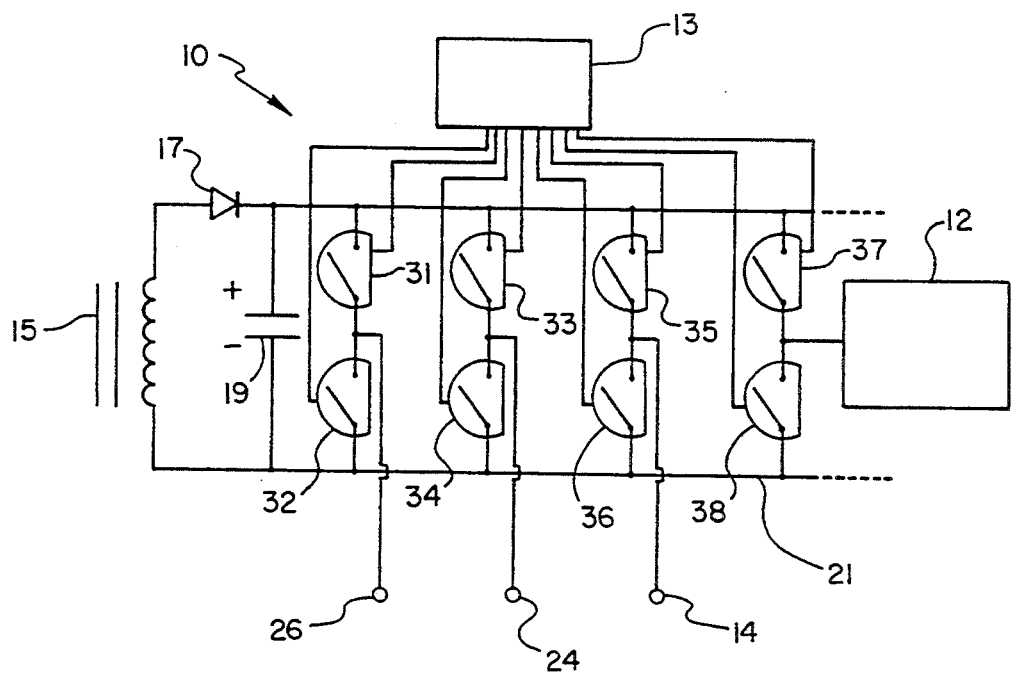
FIG. 1a illustrates schematically a simplified circuit diagram of an embodiment of the present invention.
Figure 1B:
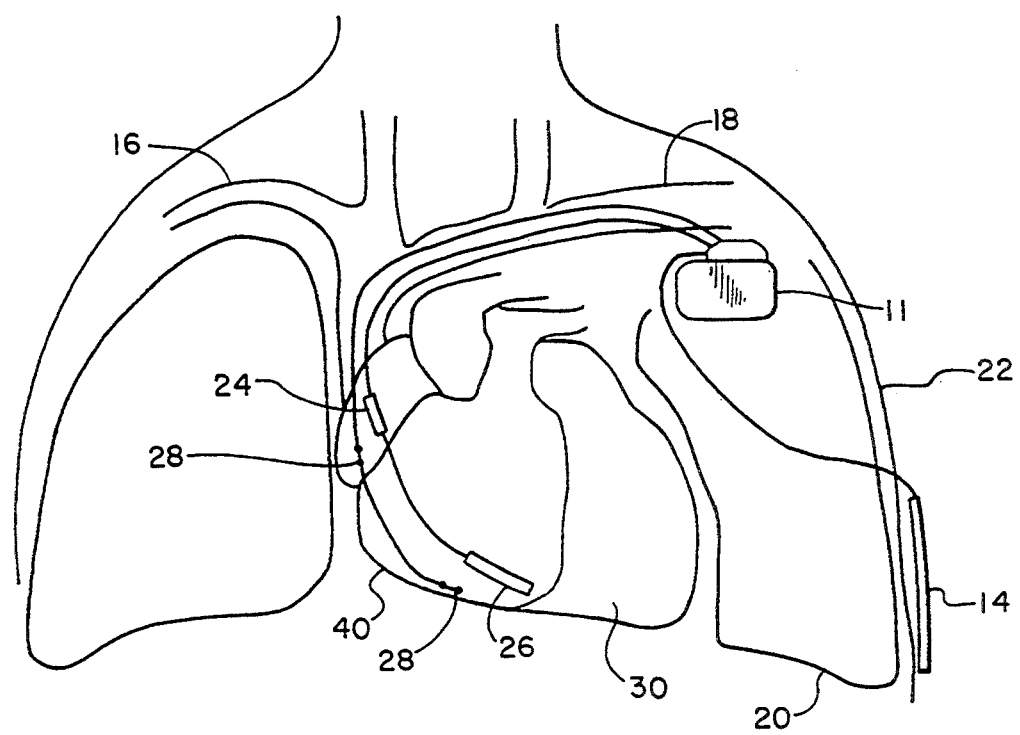
FIG. 1b illustrates schematically the location and position of the system and several electrodes within a human patient of an embodiment of the present invention.
Figure 2A:
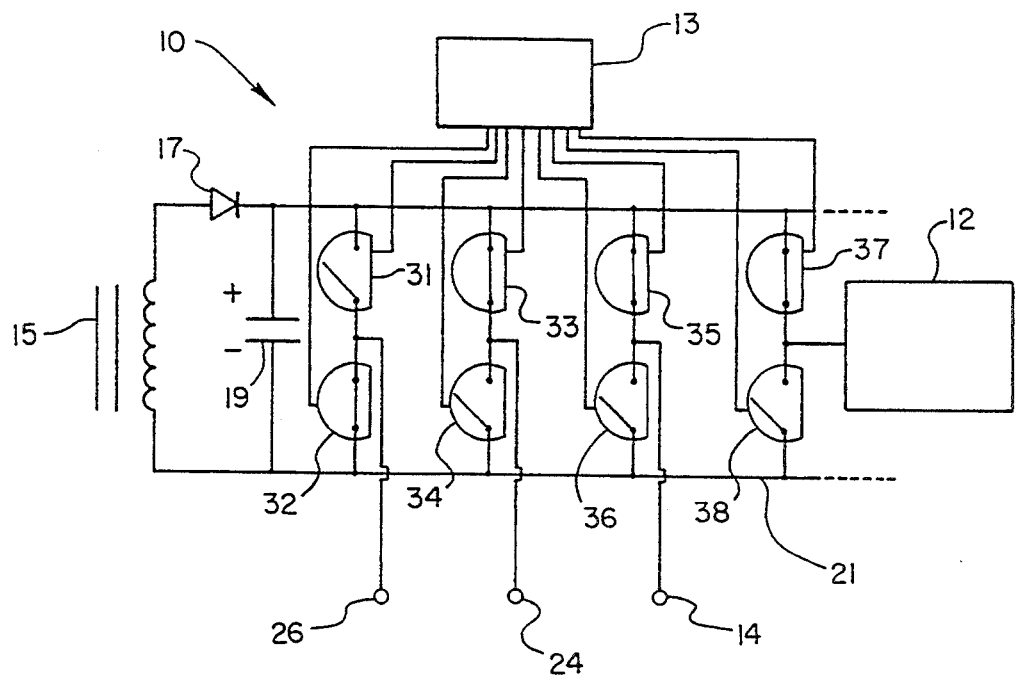
FIG. 2a illustrates schematically a simplified circuit diagram for a treatment mode of an embodiment of the present invention.
Figure 2B:
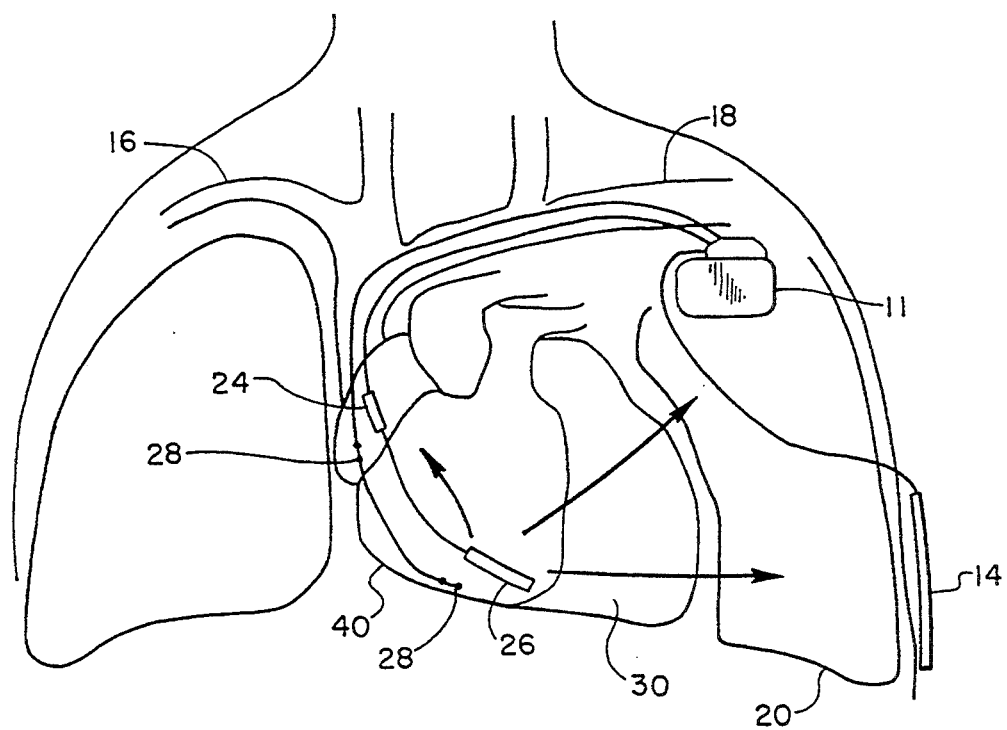
FIG. 2b illustrates schematically the location and position of the system and several electrodes within a human patient depicting the corresponding treatment mode depicted in 2a of an embodiment of the present invention.
Figure 3A:
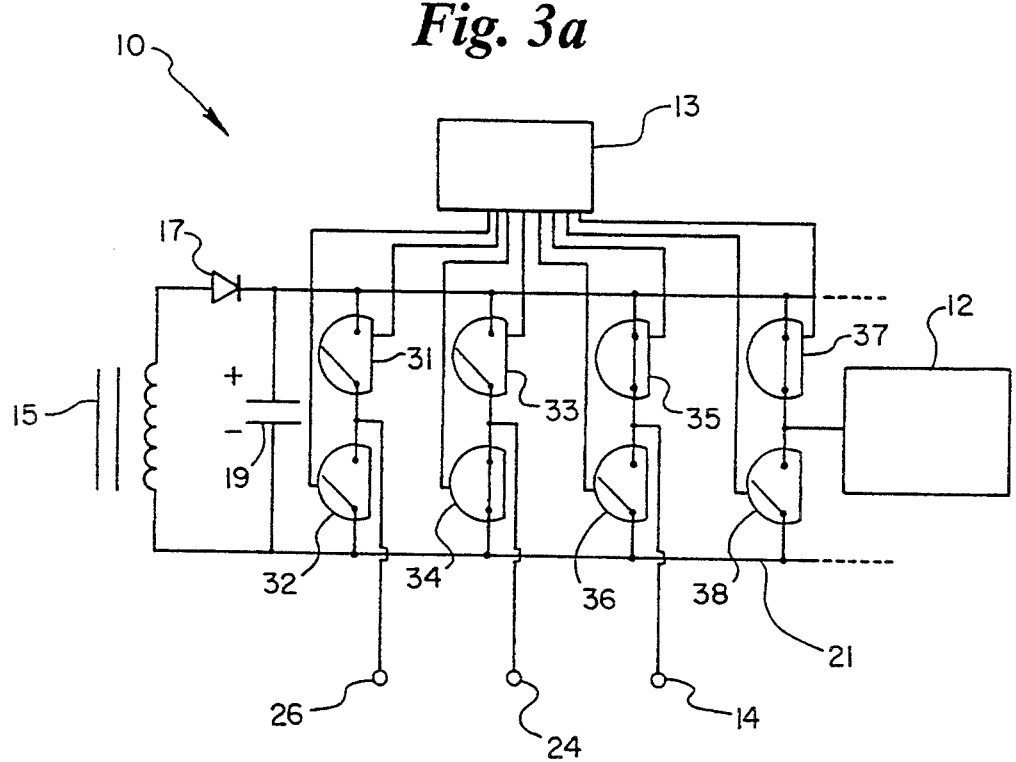
FIG. 3a illustrates schematically a simplified circuit diagram for another treatment mode of an embodiment of the present invention.
Figure 3B:
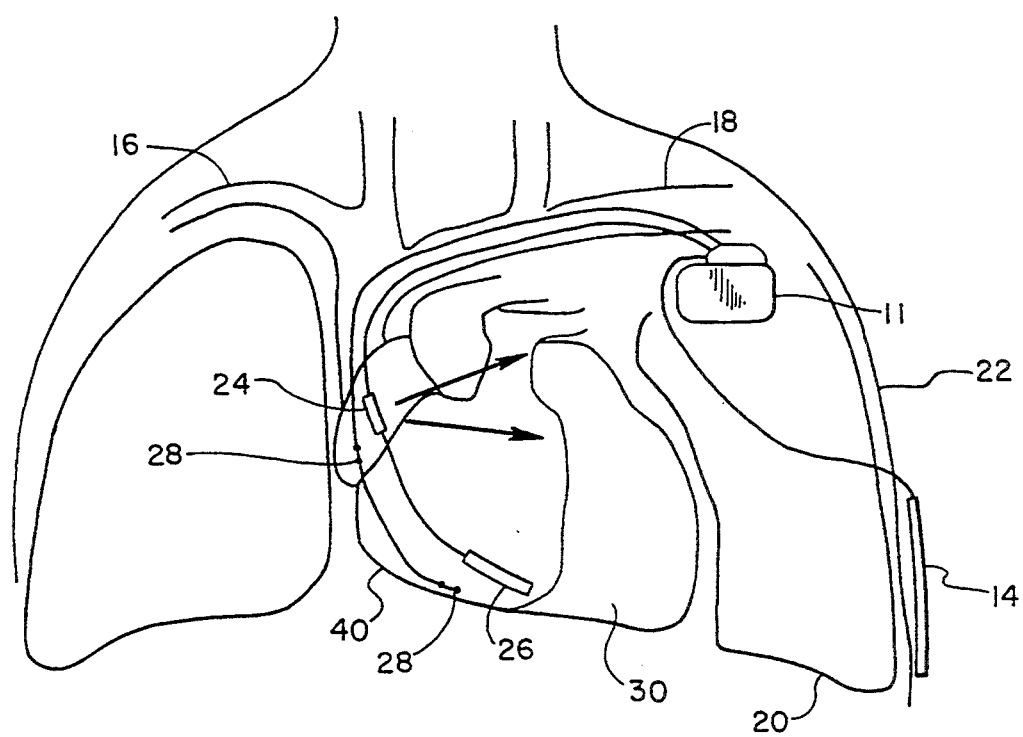
FIG. 3b illustrates schematically the location and position of the system and several electrodes within a human patient depicting the corresponding treatment mode depicted in 3a of an embodiment of the present invention.

The present invention is an implantable cardioverter defibrillator (ICD) system 10, as shown schematically in FIGS. 1a, 2a, and 3a, and shown diagrammatically in FIGS. 1b, 2b, and 3b as an embodiment of ICD system 10 as implanted within a human patient. ICD system 10 includes pulse generator can 11 which contains within its housing a source for generating an electrical charge schematically represented by transformer 15, diode 17 and capacitor 19; independently programmable switch control circuit 13; switch circuit 21; and has its surface acting as pulse generator can electrode 12.

Transformer 15 is powered by a battery source (not shown) that is also internal to pulse generator can 11. While a single physical capacitor can be used for capacitor 19, in the preferred embodiment two or more physically separate capacitors are electrically connected in series to produce an equivalent capacitance represented by capacitor 19. Alternatively, separate capacitors 19 could be used to deliver cardioversion countershocks and defibrillation countershocks, in which case independently programmable switch control circuit 13 would select the capacitor 19 from which the countershock pulse was to be delivered.

Pulse generator can 11 is implanted subcutaneously in conjunction with at least one other electrode, for example subcutaneous patch electrode 14. Pulse generator can 11 is generally placed inferior to right or left subclavicular veins 16 or 18 for ease in vascular access. Subcutaneous patch electrode 14 is placed anterolateral to the left lung 20 and chest wall 22. Heart electrodes such as right atrial 24, right ventricular 26 and pacing/sensing electrodes 28 are carried on catheters passed from pulse generator can 11 to the heart 30 via venous access.

At the time of implantation, the device is tested for efficacy by the physician. The general practice is to induce fibrillation within the patient's heart and have the ICD system attempt a defibrillation. The standard application initially configures the system such that right ventricular electrode 26 will be the anode. This configuration is chosen because of clinical success approximately 90% of the time. The advantage of the present invention is that if unsuccessful, the physician can immediately reverse the electrode polarity and administer the next countershock. If the patient is one of the 10% percent or so of patients that respond better to a reversed polarity, the physician has the latitude to program this as a preference. In this situation, the present invention saves the physician from having to remove the ICD system to perform the steps of detaching and reattaching all of the electrodes in order to achieve a polarity reversal as is the case for prior art systems. It will be seen that by providing the physician with an ICD system having independently controllable electrode discharge pathways, the physician cart selectively program at the time of implantation a wider variety of discharge pathways, polarities, and directions of each cardioversion and defibrillator countershock that is to be delivered by the device.

ICD system 10 employs switch circuit 21 consisting of a plurality of sets of switches, depicted as 31, 32, 33, 34, 35, 36, 37, and 38 in FIGS. 1a, 2a, and 3a. Depending upon the patient's practical needs to provide optimum current paths, switch circuit 21 could contain any number of sets of switches to provide control of however many cardioversion/defibrillation electrodes are used preferably on set of switches for each cardioversion/defibrillation electrode. In one embodiment of the present invention as depicted in FIGS. 1, 2, and 3, switch circuit 21 employs four separate cardioversion/defibrillation electrodes 12, 14, 24 and 26, although any number of electrodes are possible. Even numbered switches 32, 34, 36, and 38 are preferably electronic devices called metal oxide semiconducting field effect transistors (MOSFET's). Odd numbered switches 31, 33, 35, and 37 are preferably silicon controlled rectifiers (SCR's). The use of MOSFET's and SCR's permits switch circuit 21, as controlled through independently programmable switch control 13, to choose a desired discharge pathway selection by opening and/or closing switches providing the necessary control of current from capacitor 19 to the electrodes placed in the heart and body as depicted in FIGS. 1b, 2b, and 3b.

The system also utilizes pacing/sensing electrodes 28 to detect cardiac dysrhythmias, providing the diagnostic input signals to independently programmable switch control 13. Using logic and timing circuits within independently programmable switch control 13, a set of programmable switch settings that determine the cardioversion or defibrillation countershock direction, phase, duration, amplitude and polarity are configured and the countershock delivered to the heart. Following a countershock, the result is assessed and if unsuccessful, the follow up cardioversion or defibrillation countershock is modified according to changes, if any, in the programming for any one or all of the parameters and a cardioversion or defibrillation countershock is carried out again.

Figure 4:
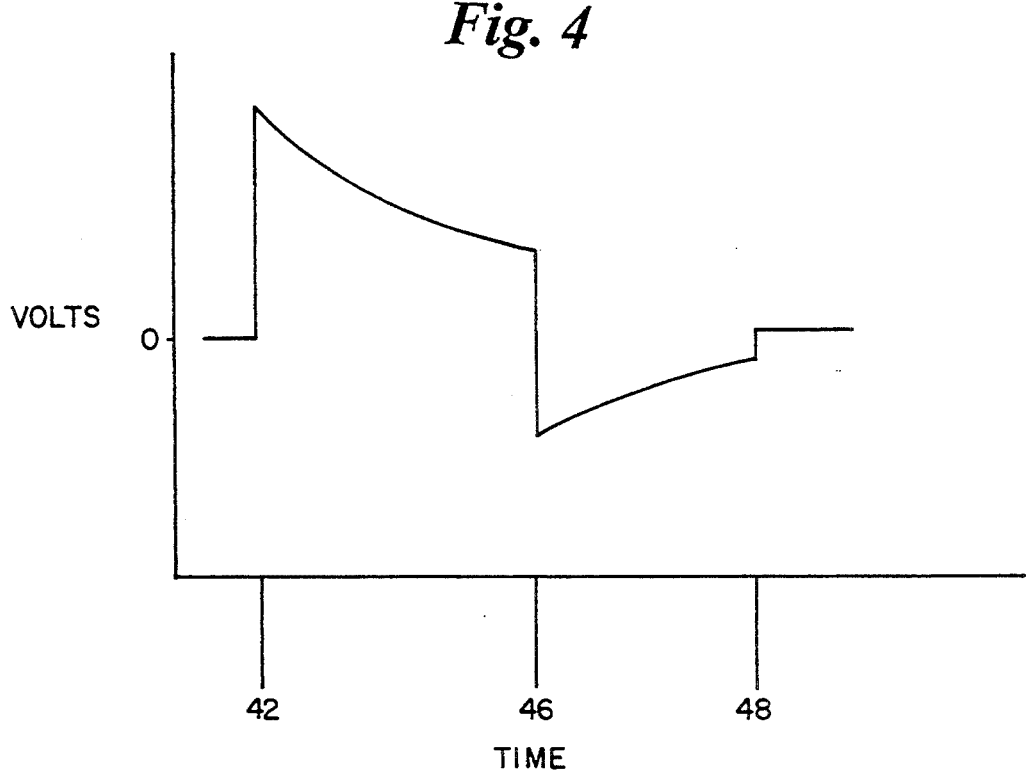
FIG. 4 illustrates a simplified graphic representation of a treatment mode of an embodiment of the present invention.

Using FIGS. 1a, 1b, and 4 and referring to switches 31, 32, 35, and 36 a bi-phasic countershock pulse can be depicted between right ventricular electrode 26 and subcutaneous patch electrode 14. The initial configuration would be to close switches 32 and 35 at the beginning of the countershock at time 42. This sets up polarity with right ventricular electrode 26 as cathode. When approximately ninety percent of the charge on capacitor 44 has been delivered at time 46, switches 32 and 35 are opened and switches 31, and 36 are closed, resulting in polarity reversal for the remainder of the countershock. Finally, switches 31 and 36 are opened at time 48 truncating the countershock.

If this initial countershock is unsuccessful, one programmed response would be to reverse the polarity, thereby the ventricular apex electrode initially starts out as an anode with switches 32 and 35 open and closing switches 31 and 36. By controlling the set of switches 31 through 38 to electrodes 12, 14, 24 and 28, the polarity of the countershock pulse is selected for either mono-phasic, bi-phasic or partial pulse. With ventricular fibrillation, the preferred countershock choice is bi-phasic for the defibrillation current as shown in FIGS. 2a and 2b, with the right ventricular electrode 26 as c. athode at the apex of the right ventricle 40. This initial setting is depicted in FIG. 4 by showing at time 42 an initial up swing of the voltage output.

Figure 6:
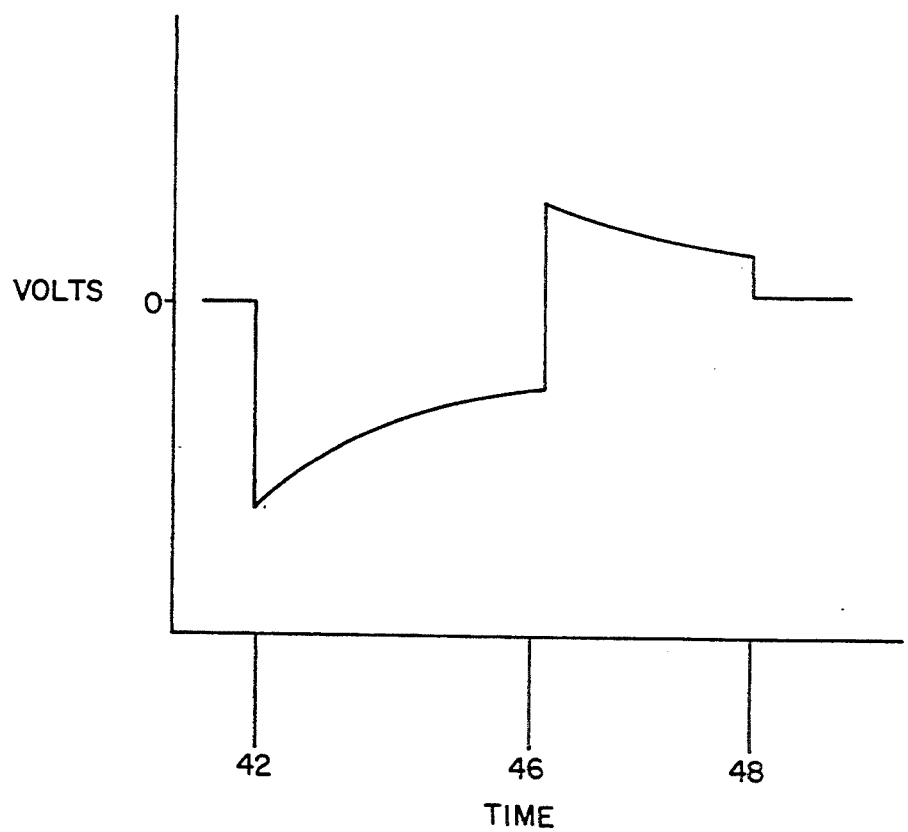
FIG. 6 illustrates a simplified graphic representation of another additional treatment mode of an embodiment of the present invention.

Under this concept of reversing the polarity, the initial polarity of right ventricular electrode 26 and subcutaneous patch electrode 14 are reversed when delivering a countershock. As shown in FIG. 6, at time 42 the initial voltage is in the reverse direction from the initial setting depicted in FIG. 4. Polarity reversal provides an alternative treatment if the prior countershock failed to defibrillate the heart. As before, the pulse can be either monophasic, bi-phasic or partial-pulse.

Figure 5:
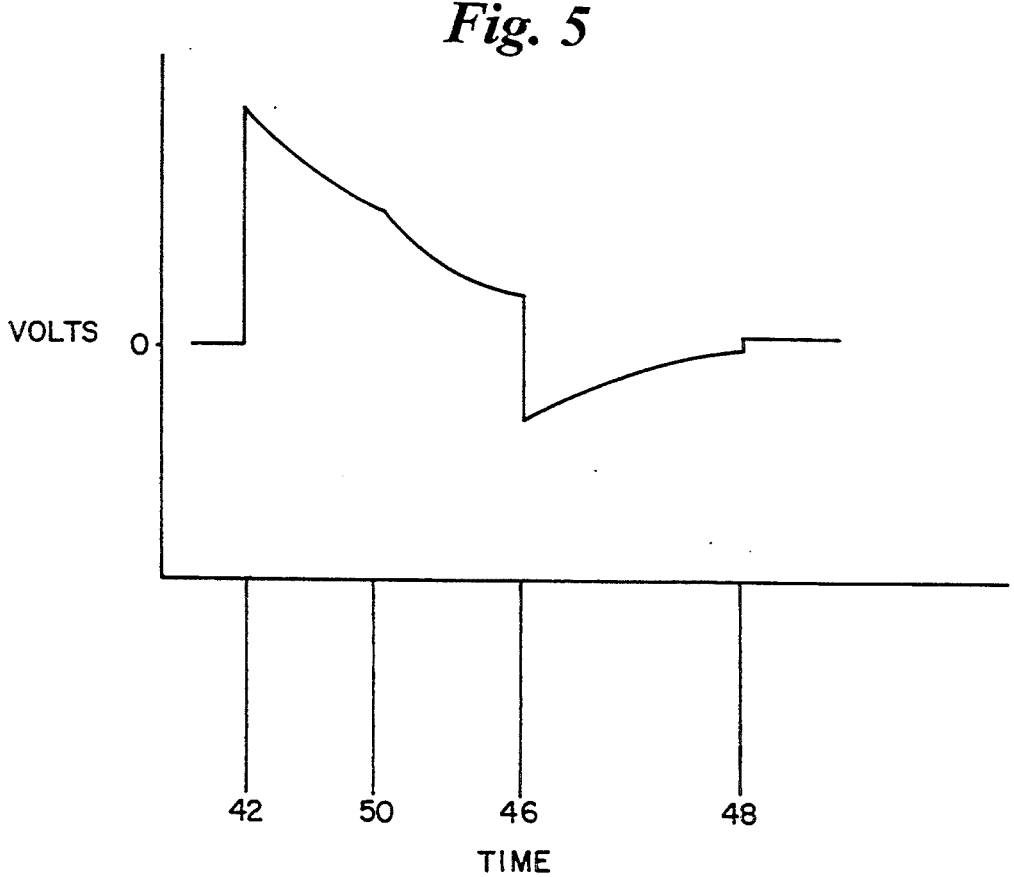
FIG. 5 illustrates a simplified graphic representation of an additional treatment mode of an embodiment of the present invention.

When the circumstance of concomitant ventricular and atrial fibrillation is encountered, the overriding concern is treatment of the ventricular fibrillation. Using FIGS. 2a, 2b, and 5, in this circumstance to configure right atrial electrode 24, practice would be to close switch 33 having right atrial electrode 24 act as an anode. Closing switch 33 could occur at the beginning of the countershock at time 42 in FIG. 5. However, because the atria require less energy to treat atrial fibrillation, depicted by the smaller open arrow, closure of switch 33 could be delayed to time 50, as shown in FIG. 5, allowing for most of the delivered countershock to traverse the ventricles first, depicted by the larger closed arrows.

A co-pending application U.S. Ser. No. 07/841,544 discloses the concept of optimal energy steering which can be implemented by the present invention. This technique allows for fine tuning energy dissipation throughout the entire heart. Depicted in the embodiment of switch circuit 21 of FIGS. 1a, 2a, and 3a, four electrodes 12, 14, 24 and 26 are enabled or disabled depending on the event detected. Switch circuit 21 allows for independent selection of cathodes and anodes to direct the countershock pulse. The programmed response for an initial configuration is adjustable. Follow-up configurations in the event the initial or subsequent countershocks fail to convert the dysrhythmia may utilize various combinations of electrodes as anode, cathode or not at all. Each of the various combinations will alter the direction and focus of the countershock, avoiding the repetition of a failed defibrillation attempt.

One example is found in the above disclosed treatment for ventricular fibrillation. Right ventricular electrode 26 acted as cathode and subcutaneous patch electrode 14 acted as anode. Configuration programming could direct that subcutaneous patch electrode 14 and pulse generator can electrode 12 are to act together as anodes. Even right atrial electrode 24 could be brought in. Any one of the electrodes could be delayed using the partial-pulse technique and any or all electrodes could have polarity reversed. The versatility of this system to carry out this programming concept is discussed below in conjunction with Tables I and II.

If atrial fibrillation is detected either in conjunction with ventricular fibrillation or arising de novo as an isolated event, the choices for switch control are similar. For isolated atrial fibrillation, and by referring to FIGS. 3a and 3b, a preferred initial configuration would have right atrial electrode 24 act as cathode in conjunction with pulse generator can electrode 12 and/or subcutaneous patch electrode 14 as anodes. A countershock of a much lower amplitude is then delivered to the atria, depicted by small closed arrows. Alternatively, the system could provide for concomitant pacing of the ventricles and timing the atrial countershock with the ventricular pacing. This method protects the ventricles from the atrial countershock by timing that countershock to be delivered at a time when the ventricles are in the absolute refractory period. For atrial fibrillation, pulse generator can electrode 12 may act as anode, with or without subcutaneous patch electrode 14 in concert, as depicted in FIG. 3b. This will allow ventricular electrode 26 to be off during all atrial fibrillation countershocks designed to treat isolated atrial fibrillation.

Figure 7:
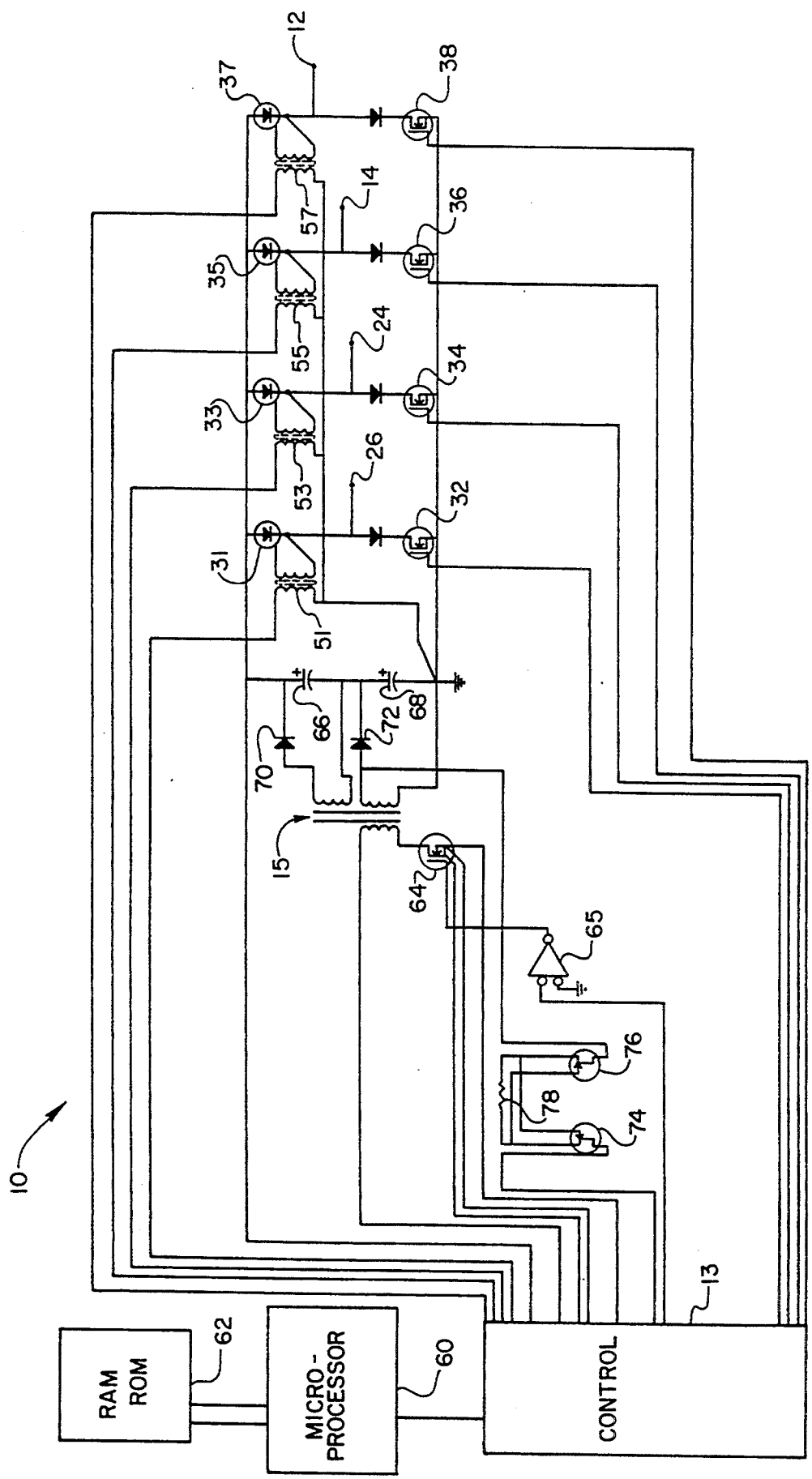
FIG. 7 illustrates a circuit schematic of a preferred embodiment of the present invention.

FIG. 7 depicts a more detailed circuit schematic of a preferred embodiment of the present invention, ICD system 10. As in FIGS. 1, 2, and 3, like numbers in FIG. 7 refer to like elements common to all the figures. SCR switches 31, 33, 35, and 37 are triggered via trigger transformers 51, 53, 55, and 57 respectively. Overall control of trigger transformers 51, 53, 55, and 57 is from independently programmable switch control 13.

The gates of MOSFET switches 32, 34, 36, and 38, however, are directly controlled through independently programmable control 13. The drains of each of MOSFET's 32, 34, 36, and 38 are electrically connected to their respective cardioversion defibrillation electrodes 26, 24, 14, and 12. The sources of each of MOSFET's 32, 34, 36, and 38 are electrically connected to the negative terminal of the power storage capacitors 66 and 68 connected in series. These SCR and MOSFET switches are regulated by independently programmable control 13 to determine which cardioversion defibrillation electrodes 12, 14, 24, and 26 will be used when and with what polarity, phase, and duration of the countershock pulse. Independently programmable control 13 houses and controls the battery source, not shown, and a communications link, also not shown, to external program control as well as receiving command signals from microprocessor 60. RAM-ROM 62 provides memory to system 10, including storing command functions, algorithms, and data collected by system 10 designated to be downloaded via an external communications link.

Independently programmable control 13 also provides, in addition to housing the battery source, control of MOSFET 64 which in turn connects the battery source to flyback transformer 15. An on/off control signal from independently programmable control 13 to the gate of MOSFET 64 is amplified by amplifier 65 ensuring that MOSFET 64 is turned on "hard" maximizing the efficiency of the charging circuit to the primary windings of flyback transformer 15. The source of MOSFET 64 is electrically connected to independently programmable control 13 and the drain of MOSFET 64 is then connected electrically to the primary windings of flyback transformer 15.

As depicted in FIG. 7, flyback transformer 15 has two secondary windings to take advantage of the two electrolytic capacitors 66 and 68 electrically connected in series. Current to capacitors 66 and 68 is rectified by diodes 70 and 72, respectively.

Dual capacitors 66 and 68 take advantage of a characteristic of electrolytic capacitors which is excellent current storage to volume ratios. This allows a smaller size which is a preferable feature for ICDs in general. Electrolytic capacitors, however, loose efficiency and eventually break down when charged beyond approximately 400 volts. Therefore, two capacitors charged to approximately 400 volts and connected in series will provide the needed high voltage output to generate the energy used in defibrillation countershock therapy.

Since various treatment modalities will require different energy outputs, ICD system 10 monitors the level of energy stored on capacitors 66 and 68 through the voltage feedback and current limiting of field effect transistors (FET) 74 and 76 connected in a back-to-back fashion. The drain of FET 76 is electrically connected to the positive terminal of a secondary winding of flyback transformer 15. The gate of FET 76 is then connected to the source of FET 74. The source of FET 76, is electrically connected in series with resistor 78 to the source of FET 74 and also electrically connected directly to the gate of FET 74. Conversely, the source of FET 74, besides being electrically connected in series with resistor 78 to the source of FET 76, is also electrically connected directly to the gate of FET 76. The drain of FET 74 is then electrically connected to independently programmable control 13. In this fashion, independently programmable control 13 is able to monitor capacitor charge voltage but is protected by the current limiting characteristics of this dual FET arrangement.

Referring to Table I, a comparison is made between the existing ICD systems and the present invention. Because the discharge pathways in existing ICD systems are fixed regardless of electrode numbers used, and because these systems only provide for phase reversal, the therapeutic choices offered by such existing ICD systems are limited to two. Table I demonstrates that the mere addition of a third electrode and the independently controllable discharge pathways of the present invention increases the number of therapeutic pathways six fold.

As shown in Table II, with the addition of a fourth electrode, the present invention realizes a geometric increase in the therapeutic countershock pathways available to the physician for programming the cardioverter/defibrillator. Table II only tabulates the therapeutic modalities for a four electrode system. The tabulation for the electrodes works as follows: when they participate as a cathode (−1), as an anode (1) or not at all (0). The present invention, as will be seen below, also provides for partialpulse and mono-phasic activity interspersed with bi-phasic activity. Therefore, whenever three or more electrodes are called upon by the system programming, the system has the additional ability to tailor some electrodes to receive a mono-phasic or partial-pulse countershock in relation to the other electrodes. Utilization of such options will depend on the dysrhythmia encountered and the treatment anticipated. These modalities, if tabulated into Table II would more than double the number of treatment options listed in the table.

Existing ICD systems developed in a direction that found it desirable to avoid bulk within the system or complexity of operation. The reasoning was to provide ,ease of operation and ease of manufacturing by supplying systems that could operate in the majority of patients. These ICD systems necessitate that placement of electrodes must be carefully planned and carefully set in order to overcome the rigidity inherent in the programming of these ICD systems. Once implanted, existing ICD systems are incapable of being changed unless replaced. Some of these systems require major surgery to implant and, thus, would require additional major surgery to replace. Most importantly, none of the existing ICD systems were capable of being tailored to the individual patient's initial or changing needs.

The individuality of the patient, plus the changing needs of the patient over time are effectively ignored by the ICD systems. Even if the original settings of such an ICD system were completely appropriate for the patient at time of implantation, subsequent conditions of the patient will change, decreasing that system's effectiveness. Being unable to anticipate change or alter the treatment, existing ICDs only continue to attempt the limited options of treatment as originally programmed, even if that treatment has proven ineffective in treating a cardiac dysrhythmic incident. that is unsuccessful.

The present invention provides flexibility of use by allowing tailored configuration programming for treatment of cardiac dysrhythmias. Physician operators are able, to easily place all electrodes and then select how each electrode will be used. If a patient's condition changes, for example through worsening cardiac disease or myocardial infarct or a heart attack, the ICD system of the present invention can be altered through reprogramming the independently controlled switching pathways to reconfigure subsequent cardioversion/-defibrillation countershocks to take into account that part of the myocardium which has died and no longer responds to an electrical stimulus. Prior art ICD systems require the replacement of the electrodes to new positions, in order to respond to these types of changed conditions, whereas the present invention allows flexibility in independently controlling any number of electrodes to allow for re-configuring the countershock electrical field obviating the need to replace any electrodes. As a result, the remaining viable myocardium can still be effectively immersed within the electric field of the countershock because this immersion is tailored spatially and temporally. Such flexibility avoids the problem of continuing to repeat an unsuccessful countershock. As experience is gained after implantation, a physician can further fine tune the patient's own system by reprogramming electrode combinations to maximize delivery of any given countershock.

Various modifications can be made to the present invention without departing from the apparent scope hereof.

TABLE 1

| Pathways of Known Methods a and c to b and d or a to b and c | | | |
|---|---|---|---|
| 1 | 1 | −1 | Ventricular Fib. (VF) |
| 2 | −1 | 1 | VF |

| Pathways of the Invention | | | |
|---|---|---|---|
| | SVC | RVA | Can |
| 1 | 1 | 1 | −1 | VF |
| 2 | 1 | 0 | −1 | Atrial Fib. (AF) |
| 3 | 1 | −1 | 1 | VF |
| 4 | 1 | −1 | 0 | AF or VF |
| 5 | 1 | −1 | −1 | AF |
| 6 | 0 | 1 | −1 | VF |
| 7 | 0 | −1 | 1 | VF |
| 8 | −1 | 1 | 1 | AF |
| 9 | −1 | 1 | 0 | AF or VF |
| 10 | −1 | 1 | −1 | VF |
| 11 | −1 | 0 | 1 | AF |
| 12 | −1 | −1 | 1 | VF |

SVC = superior vena cava
RVA = right ventricular apex
Can = pulse generator housing cannister

TABLE II

| | Electrodes | | | | Treatment |
|---|---|---|---|---|---|
| | SVC | RVA | Can | Sub Q | |
| 1 | 1 | 1 | −1 | 0 | VF |
| 2 | 1 | 0 | −1 | 0 | AF |
| 3 | 1 | −1 | 1 | 0 | VF |
| 4 | 1 | −1 | 0 | 0 | AF or VF |
| 5 | 1 | −1 | −1 | 0 | AF |
| 6 | 0 | 1 | −1 | 0 | VF |
| 7 | 0 | −1 | 1 | 0 | VF |
| 8 | −1 | 1 | 1 | 0 | VF |

TABLE II-continued

| | Electrodes | | | |
|---|---|---|---|---|
| | SVC | RVA | Can | Sub Q | Treatment |
| 9 | −1 | 1 | 0 | 0 | AF or VF |
| 10 | −1 | 1 | −1 | 0 | VF |
| 11 | −1 | 0 | 1 | 0 | AF |
| 12 | −1 | −1 | 1 | 0 | VF |
| 13 | 1 | 1 | −1 | −1 | VF |
| 14 | 1 | 1 | 0 | −1 | VF |
| 15 | 1 | 0 | −1 | −1 | AF |
| 16 | 1 | 0 | 0 | −1 | AF |
| 17 | 1 | −1 | 1 | 1 | VF |
| 18 | 1 | −1 | 0 | 1 | VF |
| 19 | 1 | −1 | −1 | 1 | VF |
| 20 | 1 | −1 | 0 | −1 | VF |
| 21 | 1 | −1 | −1 | −1 | VF |
| 22 | 0 | −1 | −1 | −1 | VF |
| 23 | 0 | 1 | 0 | −1 | VF |
| 24 | 0 | −1 | 0 | 1 | VF |
| 25 | 0 | −1 | 1 | 1 | VF |
| 26 | −1 | 1 | 1 | 1 | VF |
| 27 | −1 | 1 | −1 | 1 | VF |
| 28 | −1 | 1 | 1 | −1 | VF |
| 29 | −1 | 1 | 0 | −1 | VF |
| 30 | −1 | 1 | 0 | 1 | VF |
| 31 | −1 | 1 | −1 | −1 | VF |
| 32 | −1 | −1 | 1 | 1 | VF |
| 33 | −1 | −1 | 1 | −1 | VF |
| 34 | −1 | −1 | 0 | 1 | VF |
| 35 | −1 | −1 | −1 | 1 | VF |
| 36 | −1 | 0 | 1 | 1 | AF |
| 37 | −1 | 0 | 1 | −1 | AF |
| 38 | −1 | 0 | 0 | 1 | AF |

We claim:

1. A method for controlling a plurality of independent electrical discharge pathways to a human heart in an implantable cardioversion defibrillator system comprising the steps for:
   a) implanting at least three physically separate discharge electrodes within the human;
   b) selecting at least two electrical discharge pathways between the at least three physically separate discharge electrodes through which to deliver electrical energy to the heart;
   c) independently selecting the polarity of the electrical energy to be delivered to each of said selected discharge pathways: and
   d) independently selecting the phase of the electrical energy to be delivered to each of said selected discharge pathways.

2. The method of claim 1 wherein steps (b)–(d) are programmable for at least one cardioversion/defibrillation countershock at the time the implantable cardioversion defibrillation system is implanted.

3. The method of claim 2 further comprising:
   e) selectively reprogramming steps (b)–(d) after the implantable cardioversion system has been implanted.

4. The method of claim 2 further comprising:
   e) selectively programming steps (b)–(d) for a subsequent cardioversion/defibrillation countershock different than the programming for steps (b)–(d) for an initial cardioversion/defibrillation countershock.

5. An implantable cardioverter defibrillator system for generating and delivering cardioversion or defibrillation countershocks of greater than about 0.1 joules to a human patient in response to a sensing of a myocardial dysrhythmia in the patient, comprising:
   at least three implantation electrodes for implantation in the patient in which the at least three implantation electrodes comprise two intravascular electrodes for implantation within the heart and one electrode for implantation in the subcutaneous space proximate to the heart;
   an implantable housing to which the implantation electrodes are electrically connected, the implantable housing including:
   capacitor means for storing an electrical charge;
   means for charging the capacitor means to produce the electrical charge; and
   means for selectively controlling a discharge of the electrical charge stored in the capacitor means in response to the sensing of the myocardial dysrhythmia to generate a cardioversion/defibrillation countershock waveform, including:
      switch means for each implantation electrode for selectively electrically connecting the implantation electrode to either polarity of the capacitor means independent of the switch means for any other implantation electrode; and
      control means for selectively controlling all of the switch means to create in response to the sensing of the myocardial dysrhythmia one or more selected discharge pathways through which to deliver all or part of the waveform.

6. The system of claim 5 in which the switch means for each implantation electrode comprises a silicon controlled rectifier switch and an insulated gate bipolar transistor switch.

7. The system of claim 6 in which the control means comprises polarity control means for controlling the polarity of the countershock waveform by closing only one of either the silicon controlled rectifier switch and the insulated gate bipolar transistor switch.

8. The system of claim 7 in which the polarity control means comprises phase control means for controlling the phase of the countershock waveform by first closing one of either the silicon controlled rectifier or insulated gate bipolar transistor switches, leaving the other switch open, then reversing switch configurations during delivery of the countershock waveform.

9. The system of claim 8 in which the control means comprises delay means for simultaneously controlling the switch means by independently opening or closing each pair of switches positioned within each switch means so as to configure a desired delay in transition of the phase or the polarity of the waveform.

10. The system of claim 5 in which the at least three implantation electrodes comprise a right supraventricular electrode, a right ventricular electrode, and the implantable housing.

11. The system of claim 5 in which the control means comprises re-programming means for re-programming the control means after implantation of the apparatus.

12. The system of claim 5 in which the control means comprises:
   logic means, responsive to the sensing of myocardial dysrhythmias, for determining that a cardioversion/defibrillation has been attempted and there is a continued sensing of a myocardial dysrhythmia and providing an unsuccessful attempt signal; and
   programming means, responsive to the presence of the unsuccessful attempt signal, for providing an initial discharge sequence settings program so that the one or more selective discharge pathways are controlled to respond to the continued sensing of the myocardial dysrhythmia according to an initial response setting and the one or more selective discharge pathways are altere according to the initial discharge sequence settings program for subsequent cardioversion/defibrillation waveforms discharged in the event that the initial response setting for a cardioversion/defibrillation waveform did not successfully treat the myocardial dysrhythmias.

13. An implantable cardioverter defibrillator apparatus for generating and delivering cardioversion or defibrillation countershocks of greater than about 0.1 joules to a human patient in response to a sensing of a myocardial dysrhythmia in the patient, comprising:

at least three implantation electrodes for implantation in the patient;

an implantable housing to which the implantation electrodes are electrically connected, the implantable housing including:

capacitor means for storing an electrical charge;

means for charging the capacitor means to produce the electrical charge; and means for selectively controlling a discharge of the electrical charge stored in the capacitor means in response to the sensing of the myocardial dysrhythmia to generate a cardioversion/defibrillation countershock waveform, including:

switch means for each implantation electrode for selectively electerically connecting the implantation electrode to either polarity of the capacitor means independent of the switch means for any other implantation electrode in which each switch means comprises a silicon controlled rectifier switch and an insulated gate bipolar transistor switch; and control means for selectively controlling all of the switch means to create in response to the sensing of the myocardial dysrhythmia one or more selected discharge pathways through which to deliver all or part of the waveform.

14. The system of claim 13 in which the at least three implantation electrodes includes two intravascular electrodes for implantation within the heart and one electrode for implantation in the subcutaneous space proximate to the heart.

15. The system of claim 14 in which the electrode for implantation in the subcutaneous space is the implantable housing.

16. The system of claim 13 in which the control means comprises polarity control means for controlling the polarity of the countershock waveform by closing only one of either the silicon controlled rectifier switch and the insulated gate bipolar transistor switch.

17. The system of claim 16 in which the polarity control means comprises phase control means for controlling the phase of the countershock waveform by first closing one of either the silicon controlled rectifier or insulated gate bipolar transistor switches, leaving the other switch open, then reversing switch configurations during delivery of the countershock waveform.

18. The system of claim 17 in which the control means comprises delay means for simultaneously controlling the switch means by independently opening or closing each pair of switches positioned within each switch means so as to configure a desired delay in transition of the phase or the polarity of the waveform.

19. The system of claim 13 in which the control means comprises re-programming means for re-programming the control means after implantation of the apparatus.

20. The system of claim 13 in which the control means comprises:

logic means, responsive to the sensing of myocardial dysrhythmias, for determining that a cardioversion/defibrillation has been attempted and there is a continued sensing of a myocardial dysrhythmia and providing an unsuccessful attempt signal; and programming means, responsive to the presence of the unsuccessful attempt signal, for providing an initial discharge sequence settings program so that the one or more selective discharge pathways are controlled to respond to the continued sensing of the myocardial dysrhythmia according to an initial response setting and the one or more selective discharge pathways are altered according to the initial discharge sequence settings program for subsequent cardioversion/defibrillation waveforms discharged in the event that the initial response setting for a cardioversion/defibrillation waveform did not successfully treat the myocardial dysrhythmias.

21. An implantable cardioverter defibrillator apparatus for generating and delivering cardioversion or defibrillation countershocks of greater than about 0.1 joules to a human patient in response to a sensing of a myocardial dysrhythmia in the patient, comprising:

a) at least three implantation electrodes for implantation in the patient in which the at least three implantation electrodes comprise a right supraventricular electrode, a right ventricular electrode, and a pacing/sensing electrode;

b) capacitor means for storing an electrical charge;

c) means for charging the capacitor means to produce the electrical charge; and d) means for selectively controlling a discharge of the electrical charge stored in the capacitor means in response to the sensing of the myocardial dysrhythmia to generate a cardioversion/defibrillation countershock waveform, including:

d1) switch means for each implantation electrode for selectively electrically connecting the implantation electrode to either polarity of the capacitor means independent of the switch means for any other implantation electrode; and d2) control means for selectively controlling all of the switch means to create in response to the sensing of the myocardial dysrhythmia one or more selected discharge pathways through which to deliver all or part of the waveform.

22. The apparatus of claim 21 in which the at least three implantation electrodes includes two intravascular electrodes for implantation within the heart and one electrode for implantation in the subcutaneous space proximate to the heart.

23. The apparatus of claim 21 in which the switch means for each implantation electrode comprises a silicon controlled rectifier switch and an insulated gate bipolar transistor switch.

24. The apparatus of claim 21 in which the control means comprises polarity control means for controlling the polarity of the countershock waveform by closing only one of either the silicon controlled rectifier switch and the insulated gate bipolar transistor switch.

25. The apparatus of claim 24 in which the polarity control means comprises phase control means for controlling the phase of the countershock waveform by first closing one of either the silicon controlled rectifier or insulated gate bipolar transistor switches, leaving the other switch open, then reversing switch configurations during delivery of the countershock waveform.

26. The apparatus of claim 25 in which the control means comprises delay means for simultaneously controlling the switch means by independently opening or closing each pair of switches positioned within each switch means so as to configure a desired delay in transition of the phase or the polarity of the waveform.

27. The apparatus of claim 21 in which the control means comprises re-programming means for re-programming the control means after implantation of the apparatus.

28. The apparatus of claim 21 in which the control means comprises:

logic means, responsive to the sensing of myocardial dysrhythmias, for determining that a cardioversion/defibrillation has been attempted and there is a continued sensing of a myocardial dysrhythmia and providing an unsuccessful attempt signal; and programming means, responsive to the presence of the unsuccessful attempt signal, for providing an initial discharge sequence settings program so that the one or more selective discharge pathways are controlled to respond to the continued sensing of the myocardial dysrhythmia according to an initial response setting and the one or more selective discharge pathways are altere according to the initial discharge sequence settings program for subsequent cardioversion/defibrillation waveforms discharged in the event that the initial response setting for a cardioversion/defibrillation waveform did not successfully treat the myocardial dysrhythmias.

* * * * *